United States Patent
Jakob

(10) Patent No.: US 11,872,294 B2
(45) Date of Patent: Jan. 16, 2024

(54) PREPARATION OF SILICA-COATED CALCIUM CARBONATES WITH INCREASED SURFACE AREA AND MESOPOROSITY

(71) Applicant: IMERTECH SAS, Paris (FR)

(72) Inventor: Alexandra Jakob, Aries (FR)

(73) Assignee: Imertech SAS, Paris (FR)

( * ) Notice: Subject to any disclaimer, the term of this patent is extended or adjusted under 35 U.S.C. 154(b) by 460 days.

(21) Appl. No.: 15/733,214

(22) PCT Filed: Dec. 7, 2018

(86) PCT No.: PCT/EP2018/084006
§ 371 (c)(1),
(2) Date: Jun. 11, 2020

(87) PCT Pub. No.: WO2019/115396
PCT Pub. Date: Jun. 20, 2019

(65) Prior Publication Data
US 2021/0093518 A1 Apr. 1, 2021

(30) Foreign Application Priority Data

Dec. 12, 2017 (EP) .................................... 17306749

(51) Int. Cl.
*C09D 7/62* (2018.01)
*A61K 6/76* (2020.01)
(Continued)

(52) U.S. Cl.
CPC .............. *A61K 8/0241* (2013.01); *A61K 6/17* (2020.01); *A61K 6/60* (2020.01); *A61K 6/76* (2020.01);
(Continued)

(58) Field of Classification Search
None
See application file for complete search history.

(56) References Cited

U.S. PATENT DOCUMENTS 6,136,085 A * 10/2000 Adams, Jr. .............. C09C 1/024
428/404
2005/0244322 A1 11/2005 Chen et al.
2007/0221350 A1* 9/2007 Soga ...................... D21H 17/69
162/146

FOREIGN PATENT DOCUMENTS

EP         1736598 A1    12/2006
JP       2007070164 A  *  3/2007
WO    WO 97/40105 A1    10/1997

OTHER PUBLICATIONS

Martin A. Hubbe and Robert A. Gill. "Fillers for Papermaking: A Review of their Properties, Usage Practices, and their Mechanistic Role." Bioresources, vol. 11(1), 2016, pp. 2886-2963. (Year: 2016).*

(Continued)

*Primary Examiner* — Isaac Shomer
(74) *Attorney, Agent, or Firm* — Finnegan, Henderson, Farabow, Garrett & Dunner, LLP

(57) ABSTRACT

This disclosure describes a process for preparing silica-coated calcium carbonate particles, involving the steps of preparing an aqueous carbonate slurry containing calcium carbonate particles, adding at least one silicate composition to the aqueous carbonate slurry to obtain a carbonate-silicate slurry, lowering a pH of the carbonate-silicate slurry by adding at least one acidic compound to obtain a pH-adjusted slurry containing the silica-coated calcium carbonate particles, and isolating the silica-coated calcium carbonate particles—in which at the adding of the acidic compound is controlled such that a final pH of the pH-adjusted slurry ranges from about 7 to about 10, and the silica-coated calcium carbonate particles include a porous coating having (Continued)

an average pore diameter ranging from 2 nm to 50 nm. This disclosure also describes articles and compositions containing the silica-coated calcium carbonate particles, as well as hollow silica spheres formed from the silica-coated calcium carbonate particles.

13 Claims, 8 Drawing Sheets

(51) Int. Cl.

| | |
|---|---|
| *A61K 6/60* | (2020.01) |
| *A61K 8/19* | (2006.01) |
| *A61K 8/25* | (2006.01) |
| *A61K 8/365* | (2006.01) |
| *B01J 20/04* | (2006.01) |
| *B01J 20/10* | (2006.01) |
| *C01B 33/193* | (2006.01) |
| *D21H 17/68* | (2006.01) |
| *D21H 17/00* | (2006.01) |
| *D21H 17/67* | (2006.01) |
| *A61K 8/02* | (2006.01) |
| *C09D 7/40* | (2018.01) |
| *A61K 6/17* | (2020.01) |
| *A61K 8/11* | (2006.01) |
| *A61Q 19/00* | (2006.01) |
| *B01J 20/28* | (2006.01) |
| *C09C 1/02* | (2006.01) |
| *C09D 13/00* | (2006.01) |

(52) U.S. Cl.
CPC ............... *A61K 8/11* (2013.01); *A61K 8/19* (2013.01); *A61K 8/25* (2013.01); *A61K 8/365* (2013.01); *A61Q 19/00* (2013.01); *B01J 20/043* (2013.01); *B01J 20/103* (2013.01); *B01J 20/28021* (2013.01); *B01J 20/28059* (2013.01); *B01J 20/28061* (2013.01); *B01J 20/28083* (2013.01); *C01B 33/193* (2013.01); *C09C 1/024* (2013.01); *C09D 7/62* (2018.01); *C09D 7/70* (2018.01); *C09D 13/00* (2013.01); *D21H 17/67* (2013.01); *D21H 17/675* (2013.01); *D21H 17/68* (2013.01); *D21H 17/73* (2013.01); *A61K 2800/621* (2013.01); *A61K 2800/651* (2013.01); *C01P 2002/85* (2013.01); *C01P 2004/03* (2013.01); *C01P 2004/34* (2013.01); *C01P 2004/80* (2013.01); *C01P 2006/12* (2013.01); *C01P 2006/16* (2013.01)

(56) References Cited

OTHER PUBLICATIONS

English Translation of JP2007070164A. Obtained from Google Translate at https://patents.google.com/patent/JP2007070164A/en on Sep. 13, 2022. Originally published in Japanese on Mar. 22, 2007, pp. 1-11. (Year: 2007).*

International Search Report and Written Opinion dated Feb. 19, 2019, in International Application No. PCT/EP2018/084006 (15 pgs.).

* cited by examiner

SEM pictures (a,b), EDX mapping of Ca (c,d), EDX mapping of Si (e,f) of Socal® 31 and of PCC@SiO₂ reference.

PCC@SiO$_2$ composites at 50k (a,c,e) and 25k (b,d,f) magnifications. Acid sources: HCl (a,b), CO2 (c,d) and citric acid (e,f).

PCC@SiO$_2$ prepared with HCl without (a) and with (b) sodium heametaphosphate as a dispersant. PCC@SiO$_2$ prepared with citric acid without (c) and with (d) sodium hexametaphosphate as a dispersant.

PREPARATION OF SILICA-COATED CALCIUM CARBONATES WITH INCREASED SURFACE AREA AND MESOPOROSITY

CLAIM FOR PRIORITY

This application is a U.S. national phase entry under 35 U.S.C. § 371 from PCT International Application No. PCT/US2018/084006, filed Dec. 7, 2018, which claims the benefit of priority of European Patent Application No. 17306749.7, filed Dec. 12, 2017, from both of which this application claims priority and both of which are incorporated herein by reference.

This application relates to materials technology in general and more specifically to the preparation and use of silica-coated calcium carbonate particles having increased surface areas and mesoporosity relative to their calcium carbonate precursors.

BACKGROUND OF THE DISCLOSURE

Calcium carbonate ($CaCO_3$) is one of the most common and widely used minerals finding applications in various materials including rubbers, plastics, paint, paper, inks, food products and pharmaceuticals. Calcium carbonate particles are produced in many forms, such as precipitated calcium carbonate (PCC) and ground calcium carbonate (GCC). Modified versions of calcium carbonate are especially useful because the characteristics of this relatively-inexpensive mineral can be altered to replicate and replace other more expensive, rare or environmentally-unfriendly materials. In this context, much interest has been generated in the production and use of core-shell particles based on calcium carbonate as the core material, in which the shell of these core-shell particles is a functional surface coating.

Silica-coated calcium carbonate particles find various possible applications. For example, the hydroxyl groups that decorate the surface of silica-coated particles can be used create inter-bonds that strengthen materials such as papers, sealants and rubbers. The hydroxyl groups of silica may also serve as the basis for further chemical functionalization using, for example, silane-based surface modification agents that can radically alter the properties of the resulting surface-modified particles. Silica-coated calcium carbonates are also used as pigments and whitening agents that are found to be useful in paints and colored adhesives. However, the uses of known silica-coated calcium carbonate particles are often limited by the properties of the calcium carbonate precursor.

One problem with calcium carbonate relates to its acid sensitivity which, in most circumstances, precludes the use of calcium carbonate particles such as PCC and GCC in acidic liquids such as certain paints.

Other problems with known calcium carbonate particles relate to their relatively low surface areas and wide distribution of pore sizes. The low surface area of calcium carbonate precursors (e.g., GCC and PCC) used in known silica-coated calcium carbonate particles, generally leads to low surface areas in the resulting silica coatings. This low surface area can adversely impact the utility of known silica-coated calcium carbonate particles, for example, by limiting the concentration of reactive and/or functional groups that can decorate the surface of the particles. Wide distribution of pore sizes can adversely impact the utility of known silica-coated calcium carbonate particles, for example, by limiting the concentration of pores on the surface of the particles, which can adversely affect the sorption properties of known materials.

SUMMARY

The present inventors have recognized that a need exists to discover a process for producing silica-coated calcium carbonate particles having higher outer surface areas, narrower pore-size distributions, and increased acid resistance, relative to silica-coated calcium carbonate particles that are currently available.

The following disclosure describes the preparation and use of silica-coated calcium carbonate particles that exhibit surprisingly high outer surface areas compared to the surface areas of the precursor calcium carbonate particles. Silica-coated calcium carbonate particles of the present disclosure can also exhibit unusually sharp pore size distributions having predominantly mesoporous characteristics. Silica-coated calcium carbonate particles of the present disclosure can also exhibit increased acid resistance compared to other silica-coated calcium carbonate particles.

Embodiments of the present disclosure, described herein such that one of ordinary skill in this art can make and use them, include the following:

(1) Some embodiments relate to a process, comprising: preparing an aqueous carbonate slurry comprising calcium carbonate particles; adding at least one silicate composition to the aqueous carbonate slurry to obtain a carbonate-silicate slurry; lowering the pH of the carbonate-silicate slurry by adding at least one acidic compound to obtain a pH-adjusted slurry comprising silica-coated calcium carbonate particles; and isolating the silica-coated calcium carbonate particles, such that: the silicate composition comprises a silica and a metal oxide; a molar ratio of the silica to the metal oxide in the silicate composition ranges from 1.1:1 to 5:1; the adding of the at least one acidic compound is controlled such that a final pH of the pH-adjusted slurry ranges from about 7 to about 10; and the silica-coated calcium carbonate particles comprise a porous coating having an average pore diameter ranging from 2 nm to 50 nm;

(2) Some embodiments relate to silica-coated calcium carbonate particles obtained by the above process, wherein: the silica-coated particles comprise a calcium carbonate core at least partially covered with a silica coating; a BET surface area of the silica-coating particles ranges from 30 $m^2/g$ to 200 $m^2/g$; a ratio of the BET surface area of the silica-coated particles over a BET surface area of the calcium carbonate particle precursor of the calcium carbonate core ranges from 1.2:1 to 10:1; and an average pore diameter of the silica coating ranges from 2 nm to 50 nm; and (3) Some embodiments relate to an article or composition comprising the above silica-coated carbonate particles, wherein the article or composition is selected from the group consisting of a paper product, a sealant, a polymer, a cosmetic, a chalk, a paint, a sorption agent, a dental composition and an anti-caking agent.

Additional objects, advantages and other features of the present disclosure will be set forth in part in the description that follows and in part will become apparent to those having ordinary skill in the art upon examination of the following or may be learned from the practice of the present disclosure. The present disclosure encompasses other and different embodiments from those specifically described below, and the details herein are capable of modifications in various respects without departing from the present disclosure. In this regard, the description herein is to be understood as illustrative in nature, and not as restrictive.

BRIEF DESCRIPTION OF THE DRAWINGS

Embodiments of this disclosure are explained in the following description in view of figures that show.

DETAILED DESCRIPTION

Figures 1, 2:
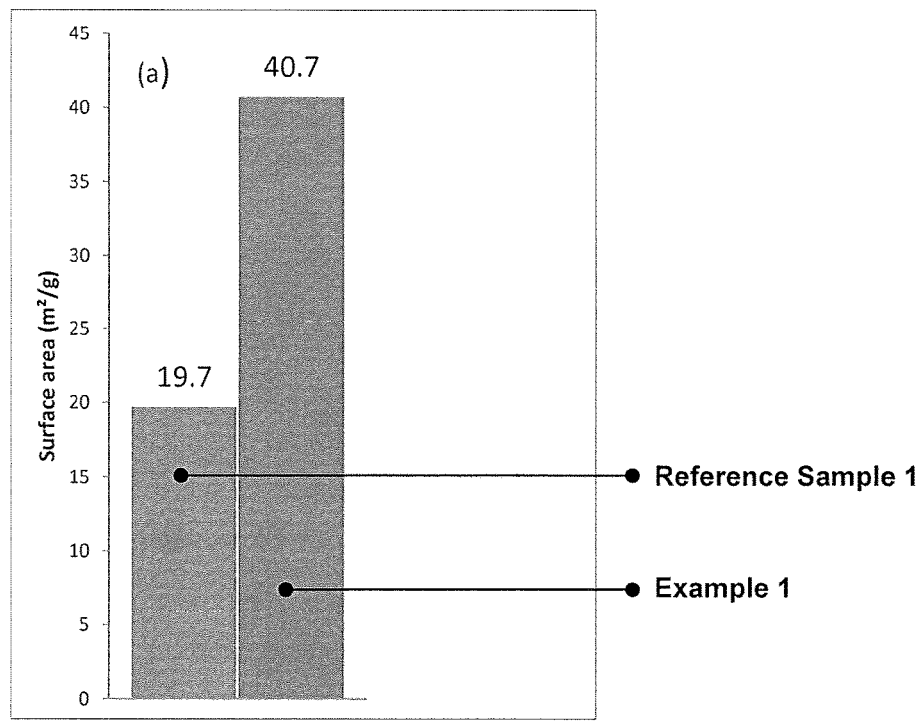
FIG. 1 is a bar chart comparing the surface area of the commercial PCC Socal® 31 versus the surface area of a silica-coated PCC formed from Socal® 31.
FIG. 2 is a graph that charts pore volume ($cm^3/g \cdot nm$) versus pore diameter (nm) for the commercial PCC Socal® 31 versus a silica-coated PCC formed from Socal® 31.
Figures 3A, 3B:
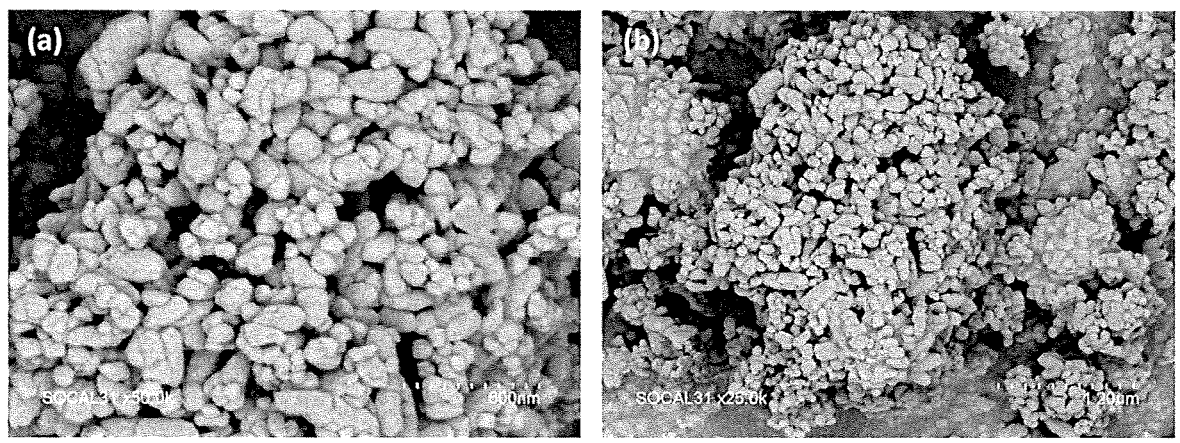
FIG. 3(a) is a SEM micrograph at 50 k magnification of the commercial PCC Socal® 31.
FIG. 3(b) is a SEM micrograph at 25 k magnification of the commercial PCC Socal® 31.
Figures 3C, 3D:
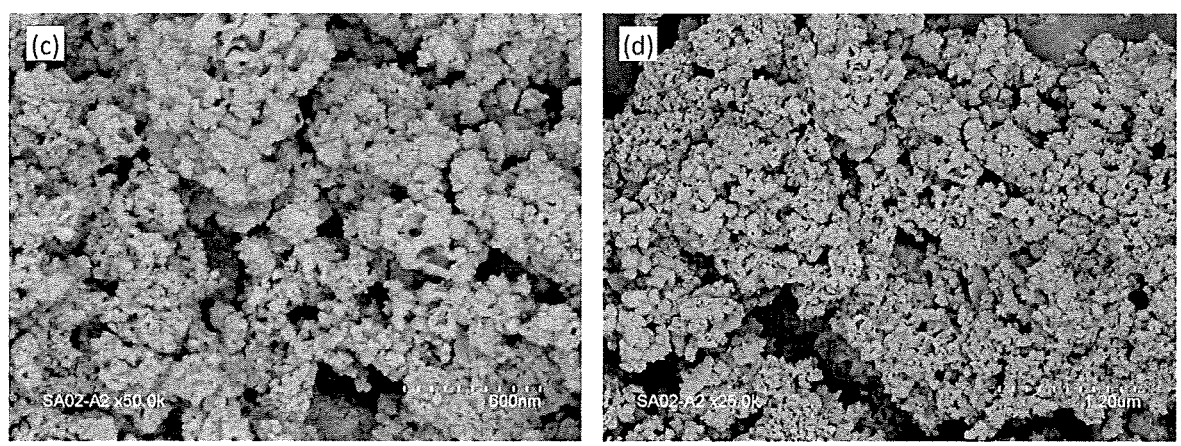
FIG. 3(c) is a SEM micrograph at 50 k magnification of a hollow silica sphere formed by treating a silica-coated PCC formed from Socal® 31 with acid.
FIG. 3(d) is a SEM micrograph at 25 k magnification of a hollow silica sphere formed by treating a silica-coated PCC formed from Socal® 31 with acid.
Figures 4A, 4B, 4C, 4D, 4E, 4F:
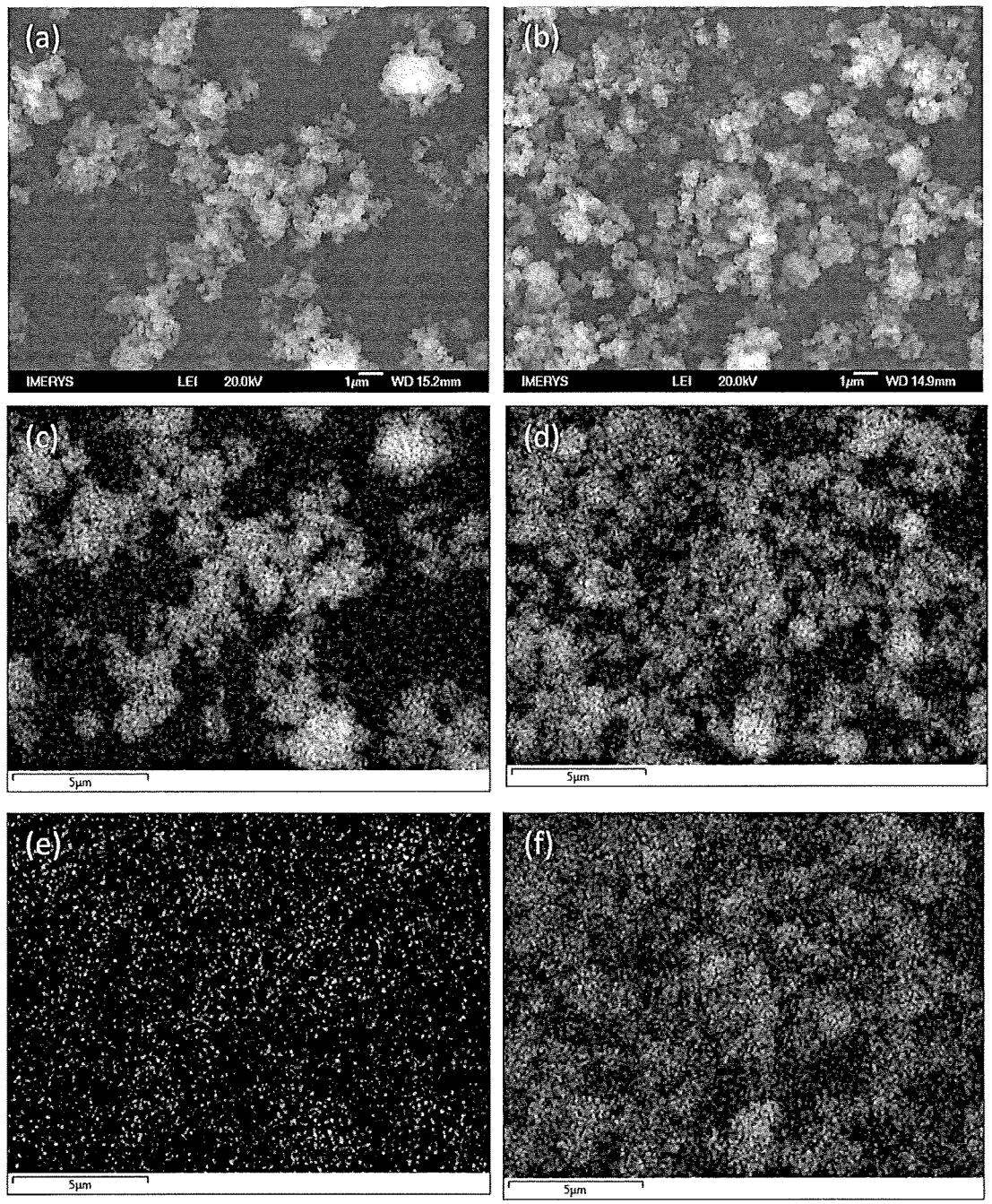
FIG. 4(a) is a SEM micrograph of the commercial PCC Socal® 31.
FIG. 4(b) is a SEM micrograph a silica-coated PCC formed from Socal® 31.
FIG. 4(c) is an energy-dispersive X-ray (EDX) map showing an elemental distribution of Ca on the surface of the commercial PCC Socal® 31.
FIG. 4(d) is an energy-dispersive X-ray (EDX) map showing an elemental distribution of Ca on the surface of a silica-coated PCC formed from Socal® 31.
FIG. 4(e) is an energy-dispersive X-ray (EDX) map showing an elemental distribution of Si on the surface of the commercial PCC Socal® 31.
FIG. 4(f) is an energy-dispersive X-ray (EDX) map showing an elemental distribution of Si on the surface of a silica-coated PCC formed from Socal® 31.

Embodiments of this disclosure includes various processes for producing silica-coated calcium carbonate particles, and the use of these particles in various applications. The terms "about" and "approximately" as used herein refer to being nearly the same as a referenced amount or value, and should be understood to encompass ±5% of the specified amount or value. The terms "mesoporous," "mesoporosity," and "mesopore" refer to materials containing pores with diameters ranging from about 2 nm to about 50 nm. In some embodiments, the silica-coated calcium carbonate particles comprise a porous coating having an average pore diameter ranging from 2 nm to 50 nm. Average pore diameter may indicate the BJH (Barrett-Joyner-Halenda) pore size (pore diameter) of the particles. The BJH pore size may be determined from the same $N_2$ adsorption isotherm that is used by the BET surface area calculations (measurement according to the BET method, AFNOR standard X11-6212 and 622 or ISO 9277). Determining the BJH pore size is described in Barrett et al., Am. Chem. Soc., 73 (1951), pages 373-380, the contents of which are incorporated herein by reference. Any suitable equipment may be used, such as the commercially available Micromeritics TRISTAR 3000 and Micromeritics VACPREP 061. The particle, before the pore size measurement, may, for example, be degassed in an oven overnight at 105° C., followed by 180° C. for 30 minutes under nitrogen flow and cooling for 30 minutes under nitrogen flow. The isotherm may, for example, be measured for relative pressures $P/P_0$ ranging from 0.05 to 0.98. Average pore size refers to pore diameter.

Some embodiments relate to a process, comprising the steps of: (1) preparing an aqueous carbonate slurry comprising calcium carbonate particles; (2) adding at least one silicate composition to the aqueous carbonate slurry to obtain a carbonate-silicate slurry; (3) lowering a pH of the carbonate-silicate slurry by adding at least one acidic compound to obtain a pH-adjusted slurry comprising silica-coated calcium carbonate particles; and (4) isolating the silica-coated calcium carbonate particles. The process is carried out such that the following conditions are satisfied: (a) the silicate composition comprises silica and a metal oxide; (b) a molar ratio of the silica to the metal oxide in the silicate composition ranges from 1.1:1 to 5:1; (c) the adding of the at least one acidic compound is controlled such that a final pH of the pH-adjusted slurry ranges from about 7 to about 10; and (d) the silica-coated calcium carbonate particles comprise a porous coating having an average pore diameter ranging from 2 nm to 50 nm.

In the step (1) of preparing the aqueous carbonate slurry, any calcium carbonate particle known in the relevant art may be used, including calcium carbonates in raw mineral form. Mixtures of different calcium carbonate particles may also be used. In some instances, the step (1) is carried out using a processed calcium carbonate such as a precipitated calcium carbonate (PCC) or a ground calcium carbonate (GCC). Any PCC or GCC known in the art may be used, and mixtures of different PCCs and/or different GCCs may also be used. PCCs may be produced by any known process, such as a lime-based process, a dry hydrated lime-based process, a $CaSO_4$-based process or a $CaCl_2$-based process. In some embodiments, the aqueous carbonate slurry is prepared using a lime-based PCC.

The polymorphism of the calcium carbonate particle may include calcite, aragonite and vaterite. In some embodiments the polymorphism of the calcium carbonate particle is limited to calcite. The elemental crystal morphology of the calcium carbonate particle may include rhomboids (pseudospherical), scalenohedron, needles, and flower like, along with various other morphologies that are much less common. In some embodiments the elemental crystal morphology of the calcium carbonate particles is limited to rhomboids.

In the step (1) of preparing the aqueous carbonate slurry, a slurry concentration of the aqueous carbonate slurry may range from about 10 g/L to about 750 g/L. In certain embodiments the slurry concentration of the aqueous carbonate slurry is limited to range from about 10-150 g/L, or from about 75-250 g/L, or from about 150-200 g/L, or from about 100-250 g/L, or from about 175-350 g/L, or from about 200-475 g/L, or from about 250-450 g/L.

The aggregation of the calcium carbonate particles in the aqueous carbonate slurry may be random or controlled. In some embodiments the step (1) of preparing the aqueous carbonate slurry is conducted such that the calcium carbonate particles in the aqueous carbonate slurry are controlled to produce nanofibers having lengths ranging from about 20 nm to about 1,000 nm. In some embodiments the lengths of the calcium carbonate nanofibers are limited to range from 40 nm to about 500 nm. In some embodiments, when the step (1) is controlled to produce calcium carbonate aggregates, the aggregate median size ($D_{50}$, measured by Sedigraph) may range from about 0.5 μm to about 50 μm, as measured using laser diffraction. In some embodiments, the step (1) is controlled such that the aggregate median size of calcium carbonate aggregates is limited to range from about 2 μm to about 25 μm.

In the step (1) of preparing the aqueous carbonate slurry, the BET surface area of calcium carbonate particles may range from about 2 $m^2/g$ to about 200 $m^2/g$. In some embodiments the aqueous carbonate slurry is prepared in a manner such that the BET surface area of the calcium carbonate particles is limited to range from about 1 $m^2/g$ to about 80 $m^2/g$, or in other embodiments from about 1 $m^2/g$ to about 25 $m^2/g$. As illustrated in experimental section that follows, it was discovered that using a process of this disclosure can lead to a significant increase in the BET surface area of the silica-coated calcium carbonate particles relative to the BET surface area of the calcium carbonate particles used to prepare the aqueous carbonate slurry. The calcium carbonate particles may be mesoporous, or may not be mesoporous.

In the step (1) of preparing the aqueous carbonate slurry, the calcium carbonate particles may be surface-treated calcium carbonate particles. Surface modifying agents may include, by non-limiting example, silicon-containing compounds such as silicones and silanes, polyacrylates, EDTA, and other surface modifying agents known in the art. Silicon-containing surface modifying agents may contain additional functional groups such as alkylene groups, alkoxy groups, amino groups, aryl groups, carbamate groups, epoxy groups, ester groups, ether groups, halide groups, heteroaryl groups, sulfide and/or disulfide groups, hydroxyl groups, isocyanate group, nitrile groups, ionic (charged) groups, and mixtures thereof. Examples of suitable surface modification agents are mono- and polycarbonic acids, corresponding acid anhydrides, acid chlorides, esters and acid amides, alcohols, alkyl halides, amino acids, imines, nitriles, isonitriles, epoxy compounds, mono- and polyamine, dicarbonyl compounds, silanes and metal compounds. In some embodiments the surface modification agents containing a hydrophobic and/or oleophobic group may include silanes, carbonic acids, carbonic acid derivatives such as acid anhydrides and acid halides, in particular acid chlorides, alcohols, alkyl halides such as alkyl chlorides, alkyl bromides and alkyl iodides, wherein the alkyl residue may be substituted in particular with fluorine.

In the step (1) of preparing the aqueous carbonate slurry, the aqueous medium may include only water, or the aqueous medium may include water and an additional agent such as a dispersant. Suitable dispersants may be selected from conventional dispersant materials commonly used in the processing of alkali earth metal carbonates. Such dispersants will be recognized by those skilled in this art. Dispersants are generally water-soluble salts capable of supplying anionic species, which in their effective amounts may adsorb on the surface of the alkali earth metal carbonate particles and thereby inhibit aggregation of the particles. The unsolvated salts suitably include alkali metal cations, such as sodium. Examples of suitable dispersants also include water soluble condensed phosphates, for example, polymetaphosphate salts (general form of the sodium salts: $(NaPO_3)_x$), such as tetrasodium metaphosphate or so-called "sodium hexametaphosphate" (Graham's salt), water-soluble salts of polysilicic acids; polyelectrolytes; salts of homopolymers or copolymers of acrylic acid or methacrylic acid; or salts of polymers of other derivatives of acrylic acid, suitably having a weight average molecular mass of less than about 20,000. In some embodiments the step (1) of preparing the aqueous carbonate slurry involves the use of an aqueous medium containing sodium hexametaphosphate and/or a sodium polyacrylate, the latter suitably having a weight average molecular mass in the range of about 1,500 to about 10,000.

In some embodiments the process includes an additional step of adding a dispersant to at least one of the aqueous carbonate slurry, the carbonate-silicate slurry, and the pH-adjusted slurry. The added dispersant may include one or more dispersants as described above. In some cases, the added dispersant is selected from an organic acid, a carbohydrate compound, a metal salt, and mixtures thereof.

In the step (1) of preparing the aqueous carbonate slurry, the calcium carbonate particles may be at least partially coated with an organic compound such as, but not limited to, citric acid or a sugar. For example, in some embodiments the calcium carbonate particles are at least partially coated with a carbohydrate. In some embodiments the calcium carbonate particles are at least partially coated with an organic dispersant or chelating agent such as, but not limited to, sodium hexametaphosphate.

In the step (2) of preparing the carbonate-silicate slurry, the silicate composition may include a lithium silicate, a sodium silicate, a potassium silicate or various mixtures thereof. In some embodiments the silicate composition may be a composition containing a silica ($SiO_2$) and an oxide of at least one metal selected from an alkali metal and an alkaline earth metal. For example, the metal oxide may be at least one metal oxide selected $Li_2O$, $Na_2O$ and $K_2O$. A molar ratio of the silica to the metal oxide in the silicate composition may range from about 1:1 to about 5:1. In some embodiments the carbonate-silicate slurry is prepared using a silicate composition in which the molar ratio of the silica to the metal oxide ranges from about 3:1 to about 4:1. The silicate composition added to the aqueous carbonate slurry may be in a liquid phase or in a solid phase. The silicate composition may be in the form of a silicate solution or slurry comprising water, the silica and the metal oxide, in which a concentration of the silica in the silicate solution or slurry ranges from about 0.5 mol/L to about 10 mol/L. In some embodiments the concentration of the silicate solution or slurry ranges from about 1.0 mol/L to about 1.5 mol/L.

In the step (2) of preparing the carbonate-silicate slurry, the silicate composition may be in the form of a liquid composition of silica and sodium oxide ($Na_2O$) in which the liquid composition has a density ranging from about 1.2 $kg/m^3$ to about 2.0 $kg/m^3$, or may be in the form of a solid composition of silica and sodium oxide in which the solid composition has a density ranging from about 0.4 $kg/m^3$ to about 1.6 $kg/m^3$, or may be in the form of a solid composition of silica and lithium oxide ($Li_2O$) in which the solid composition has a density ranging from about 1.1 $kg/m^3$ to about 1.5 $kg/m^3$, or may be in the form of a solid composition of silica and potassium oxide ($K_2O$) in which the solid composition has a density ranging from about 1.1 $kg/m^3$ to about 1.5 $kg/m^3$. In some embodiments the silica composition contains silica and sodium oxide and has a density ranging from about 1.3 $kg/m^3$ to about 1.5 $kg/m^3$.

In the step (2) of preparing the carbonate-silicate slurry, the silicate composition may be a sodium silicate compositions containing 15-35 weight % of silica and 5-35 weight % of sodium oxide, or may be a lithium silicate composition containing 15-35 weight % of silica and 1-10 weight % of lithium oxide, or may be a potassium silicate composition containing 15-35 weight % of silica and 5-20 weight % of potassium oxide. In some embodiments the silica composition is limited to a sodium silicate composition containing 25-30 weight % of silica and 5-10 weight % of sodium oxide.

In the step (2) of preparing the carbonate-silicate slurry, a molar ratio of calcium carbonate to silica in the carbonate-silicate slurry may range from about 1:1 to about 100:1. In some embodiments the molar ratio of calcium carbonate to silica in the carbonate-silicate slurry is limited to range from about 1.5:1 to about 5:1.

In the step (2) of preparing the carbonate-silicate slurry, the addition of the silica composition to the aqueous carbonate slurry may occur such that the temperature of the aqueous carbonate slurry is controlled to range from about 15° C. to about 95° C. In some embodiments the temperature of the aqueous carbonate slurry during the addition step is controlled to range from about 20° C. to about 25° C. During the addition step (2), the silicate composition may be added continuously or may be added in dropwise fashion. In some embodiments the silicate composition is added to the aqueous carbonate slurry at an addition rate that ranges from about 1.7 to about 255 or from about 8.5 to about 25.5 (mole of silicate per minute) per kiloliter of the aqueous carbonate slurry. During the addition of the silicate composition to the aqueous carbonate slurry, the aqueous carbonate slurry may be stirred at a rate of up to 1,000 rpm. In some embodiments the stirring rate may be limited to range from about 600 rpm to about 800 rpm. In some embodiments the mode of addition may be altered such that the aqueous carbonate slurry is added to the silicate composition.

In the step (3) of lowering the pH of the carbonate-silicate slurry, the acidic compound may be a strong acid such as hydrochloric acid, nitric acid, sulfuric acid, hydrobromic acid or hydroiodic acid, as well as other strong acids known in the art, or a weak acid such as a carboxylic acid, phosphoric acid, boric acid or hydrofluoric acid, as well as other weak acids known in the art. In some embodiments the acidic compound is hydrochloric acid, which may be used in gaseous form and may be used as an aqueous or non-aqueous solution. A concentration of hydrochloric acid solution used as the acidic compound may range from about 0.1 M to 12 M (i.e., concentrated aqueous concentrated HCl). In some embodiments the acidic compound comprises an acid having a pKa of less than 2.

In the step (3) of lowering the pH of the carbonate-silicate slurry, the acidic compound may be an organic acid having a pKa of equal to or greater than 2. For example, in some embodiments the acidic compound comprises at least one water-soluble organic carboxylic acid selected from a monocarboxylic acid, a dicarboxylic acid, a tricarboxylic acid, and salts thereof. The acidic compound may comprise a water-soluble hydroxycarboxylic acid or a salt thereof. For example, the acidic compound may comprise at least one organic acid selected from formic acid, glyoxylic acid, oxalic acid, glycolic acid, malonic acid, 3-hydroxypropanoic acid, lactic acid, glyceric acid, fumaric acid, maleic acid, oxaloacetic acid, 3-butenoic acid, crotonic acid, methylmalonic acid, succinic acid, malic acid, tartaric acid, dihydroxytartaric acid, butanoic acid, 3-hydroxybutanoic acid, 4-hydroxybutanoic acid, 1,1-cyclopropane dicarboxylic acid, itaconic acid, mesaconic acid, dimethylmalonic acid, glutaric acid, methylsuccinic acid, pentanoic acid, ascorbic acid, citric acid, isocitric acid, 3-methylglutaric acid, hexanoic acid and salts thereof.

In the step (3) of lowering the pH of the carbonate-silicate slurry, the acidic compound may be a water-soluble $C_2$-$C_{30}$ aliphatic and/or aromatic organic acid, in which aliphatic acids may be fully saturated or may be unsaturated. The acidic compound may include salts or mixtures of free acids and salts. In some embodiments the acidic compound may include a polymeric acid, such as polymeric acids prepared from ethylenenically unsaturated carboxylic monomers including, for example, acrylic acid, methacrylic acid, fumaric acid, and maleic acid. These polymers may have weight average molecular weights of less than about 1,000,000, or less than 50,000, as determined by light scattering techniques.

In some embodiments the acid compound is selected from phosphoric acid, metaphosphoric acid, hexametaphosphoric acid, ethylenediaminetetraacetic acid (EDTA), sulfurous acid, acetic acid, boric acid, gallic acid, glutaric acid, benzoic acid, oxybenzoic acid, salicyclic acid, citric acid, formic acid, fluoroboric acid and mixtures thereof. Mixtures of these acids, as well as other acids described above, may be combined with the use of carbon dioxide during the step (3) of lowering the pH of the carbonate-silicate slurry. In some embodiments at least one buffering acid may serve as the acidic compound, or may be included as a component of the acidic compound. For example, in some embodiments the acidic compound includes citric acid as a weak, buffering acid.

In the step (3) of lowering the pH of the carbonate-silicate slurry, the addition of the acidic compound to the carbonate-silicate slurry may occur such that the temperature of the carbonate-silicate slurry ranges from about 15° C. to about 95° C. In some embodiments the temperature of the carbonate-silicate slurry during the addition of the acidic compound is controlled to range from about 20° C. to about 25° C. The carbonate-silicate slurry may be stirred during the addition of the acidic compound, such that the rate of stirring is less than or equal to 1,000 rpm. In some embodiments the rate of stirring of the carbonate-silicate slurry during the addition of the acidic compound is controlled to range from about 600 rpm to about 800 rpm. The acid compound may be added continuously or by dropwise addition, in which the rate of dropwise addition may range from about 1.7 to about 255 or from about 8.5 to about 25.5 (mole of acid compound per minute) per kiloliter of the carbonate-silicate slurry. The rate of addition of the acid compound, the rate of stirring of the carbonate-silicate slurry, and the temperature of the carbonate-silicate slurry may be controlled in order to prevent or minimize gelling during the step (3) of lowering the pH of the carbonate-silicate slurry.

In the step (3) of lowering the pH of the carbonate-silicate slurry, the amount of the acid compound may be controlled such that the molar ratio of the calcium carbonate to acid groups in the acid compound ranges from about 100:1 to about 1:1. In some embodiments the molar ratio of the calcium carbonate to the acid compound is limited to range from about 9:1 to about 4:1.

In the step (3) of lowering the pH of the carbonate-silicate slurry, the final pH of the pH-adjusted slurry may range from about 7 to about 9, or from about 7 to about 8, or from about 7 to about 7.5. In some embodiments the final pH of the pH-adjusted slurry is approximately 7.

The process of forming the silica-coated calcium carbonate particles may include an additional step of aging the pH-adjusted slurry over period ranging from 1 to 150 minutes. In some embodiments the aging of the pH-adjusted slurry occurs at a temperature ranging from 15° C. to 95° C., and may occur with stirring of the pH-adjusted slurry at rate ranging from about 1 rpm to about 1,000 rpm. In some embodiments the aging of the pH-adjusted slurry is controlled such that the temperature of the pH-adjusted slurry ranges from about 60° C. to about 80° C. Aging of the pH-adjusted slurry may occur over a period ranging from 1 min to about 150 minutes, in which some embodiments are limited such that the period of aging ranges from about 90 minutes to about 120 minutes.

The step (4) of isolating the silica-coated calcium carbonate particles may include the steps filtering, washing, drying and/or milling the silica-coated carbonate particles—but is not limited to these steps. In some embodiments the washing of the silica-coated carbonate particles includes at least one of (i) washing a filter cake of the silica-coated calcium carbonate particles with a washing liquid, and (ii) dispersing the silica-coated carbonate particles into the washing liquid, and then filtering the silica-coated carbonate particles from the washing liquid. The washing liquid contains water and optionally a dispersant and/or detergent. In some embodiments the performing of the steps (i) and/or (ii) above can lead to the formation of silica-coated calcium carbonate particles having improved characteristics relative to silica-coated calcium carbonate particles not obtained by performing the steps (i) and/or (ii) above. For example, in some embodiments the performing of the steps (i) and/or (ii) may increase the BET surface area of the silica-coated calcium carbonate particles, or may increase the mesoporosity of the silica-coated calcium carbonate particles. In some embodiments, at least one of the steps (i) and (ii) may be performed at least two times.

In the step (4) of isolating the silica-coated calcium carbonate particles, the drying may occur at a temperature ranging from about 50° C. to about 200° C. In some embodiments the drying occurs at a temperature ranging from about 80° C. to about 120° C. Milling of the silica-coated calcium carbonate particles may be carried out using a pin mill, a hammer mill or a classifier mill.

Some embodiments of the present disclosure relate to silica-coated calcium carbonate particles obtained by the process described above. A silica-coated calcium carbonate particle of the present disclosure may include a calcium carbonate core at least partially covered with a silica coating, in which at least one of the following characteristics is satisfied: (a) a BET surface area of the silica-coating calcium carbonate particle ranges from about 30 $m^2/g$ to about 200 $m^2/g$; (b) a ratio of the BET surface area of the silica-coated calcium carbonate particle over a BET surface area of a calcium carbonate particle precursor of the calcium carbonate core ranges from about 1.1:1 to about 80:1; and (c) an average pore diameter of the silica coating ranges from 2 nm to 50 nm. In some embodiments the BET surface area of the silica-coated calcium carbonate particle ranges from about 50 $m^2/g$ to about 80 $m^2/g$. The average pore size of the silica-coated calcium carbonate particle may range from about 5 nm to about 20 nm, and the ratio (b) may range from about 2:1 to about 6:1.

Some embodiments of the present disclosure relate to an article or composition containing silica-coated carbonate particles obtained by the process described above. The article or composition may be a paper product, an adhesive, a sealant, a polymer, a cosmetic, a chalk, a paint, a sorption agent, a dental composition or an anti-caking agent, just to name a few applications. Applications of the silica-coated carbonate particles may also include water purification materials, water sludge treatment materials, carrier agents for cosmetics or agricultural applications, oral compositions, and odor controls agents, just to name a few. Embodiments of the present disclosure also include hollow silica sphere's obtained by treating the silica-coated calcium carbonate particles with an acidic composition.

EMBODIMENTS

Embodiment [1] of the present disclosure relates to a process, comprising: preparing an aqueous carbonate slurry comprising calcium carbonate particles; adding at least one silicate composition to the aqueous carbonate slurry to obtain a carbonate-silicate slurry; lowering a pH of the carbonate-silicate slurry by adding at least one acidic compound to obtain a pH-adjusted slurry comprising silica-coated calcium carbonate particles; and isolating the silica-coated calcium carbonate particles, wherein: the silicate composition comprises a silica and a metal oxide; a molar ratio of the silica to the metal oxide in the silicate composition ranges from 1.1:1 to 5:1; the adding of the at least one acidic compound is controlled such that a final pH of the pH-adjusted slurry ranges from about 7 to about 10; and the silica-coated calcium carbonate particles comprise a porous coating having an average pore diameter ranging from 2 nm to 50 nm.

Embodiment [2] of the present disclosure relates to the process of Embodiment [1], wherein the calcium carbonate particles are selected from the group consisting of precipitated calcium carbonate particles, ground calcium carbonate particles, waste calcium carbonate particles, and mixtures thereof.

Embodiment [3] of the present disclosure relates to the process of Embodiment [1] or [2], wherein the calcium carbonate particles are at least partially coated with an organic compound comprising at least one hydroxyl group.

Embodiment [4] of the present disclosure relates to the process of Embodiments [1]-[3], further comprising adding a dispersant to at least one of: the aqueous carbonate; the carbonate-silicate slurry; and the pH-adjusted slurry.

Embodiment [5] of the present disclosure relates to the process of Embodiments [1]-[4], wherein: the silicate composition comprises the silica and an oxide of at least one metal selected from the group consisting of an alkali metal and an alkaline earth metal; a molar ratio of the silica to the metal oxide ranges from 1.1:1 to 5:1; and a molar ratio of the silica to the calcium carbonate in the carbonate-silicate slurry ranges from 1:1 to 1:100.

Embodiment [6] of the present disclosure relates to the process of Embodiments [1]-[5], wherein the acidic compound comprises at least one of: an organic acid having a pKa of equal to or greater than 2; and an acidic composition comprising an acid having a pKa of less than 2.

Embodiment [7] of the present disclosure relates to the process of Embodiments [1]-[6], wherein the acidic compound comprises a water-soluble hydroxycarboxylic acid or a salt thereof.

Embodiment [8] of the present disclosure relates to the process of Embodiments [1]-[7], wherein the acidic compound comprises at least one selected from the group consisting of formic acid, glyoxylic acid, oxalic acid, glycolic acid, malonic acid, 3-hydroxypropanoic acid, lactic acid, glyceric acid, fumaric acid, maleic acid, oxaloacetic acid, 3-butenoic acid, crotonic acid, methylmalonic acid, succinic acid, malic acid, tartaric acid, dihydroxytartaric acid, butanoic acid, 3-hydroxybutanoic acid, 4-hydroxybutanoic acid, 1,1-cyclopropanedicarboxylic acid, itaconic acid, mesaconic acid, dimethylmalonic acid, glutaric acid, methylsuccinic acid, pentanoic acid, ascorbic acid, citric acid, isocitric acid, 3-methylglutaric acid, hexanoic acid and salts thereof.

Embodiment [9] of the present disclosure relates to the process of Embodiments [1]-[8], wherein the adding of the at least one acidic compound to the carbonate-silicate slurry is controlled such that the final pH of the pH-adjusted slurry ranges from about 7 to about 7.5.

Embodiment [10] of the present disclosure relates to the process of Embodiments [1]-[9], further comprising: aging the at least partially neutralized carbonate-silicate slurry at a temperature ranging from 15° C. to 95° C. over a period ranging from 10 minutes to 120 minutes.

Embodiment [11] of the present disclosure relates to the process of Embodiments [1]-[10], wherein the isolating comprises filtering, washing, drying and milling the silica-coated carbonate particles.

Embodiment [12] of the present disclosure relates to the process of Embodiments [1]-[11], wherein: the isolating comprises filtering, washing, drying and milling the silica-coated carbonate particles, such that the washing comprises at least one of (i) washing a filter cake of the silica-coated calcium carbonate particles with a washing liquid, and (ii) dispersing the silica-coated carbonate particles into the washing liquid, filtering the silica-coated carbonate particles from the washing liquid; and the washing liquid comprises water and optionally a dispersant or detergent.

Embodiment [13] of the present disclosure relates a silica-coated calcium carbonate particle obtained by a process of Embodiments [1]-[12], wherein the silica-coated particle comprising a calcium carbonate core at least partially covered with a silica coating, and wherein: a BET surface area of the silica-coating particle ranges from 30 $m^2/g$ to 200 $m^2/g$; a ratio of the BET surface area of the silica-coated particle over a BET surface area of a calcium carbonate particle precursor of the calcium carbonate core ranges from 1:1 to 10:1; and an average pore diameter of the silica coating ranges from 2 nm to 50 nm.

Embodiment [14] relates to an article or composition comprising the silica-coated carbonate particle of Embodiment [13], wherein the article or composition is selected from the group consisting of a paper product, a sealant, a polymer, a cosmetic, a chalk, a paint, a sorption agent, a dental composition and an anti-caking agent.

Embodiment [15] relates to a hollow silica sphere obtained by contacting the silica-coated calcium carbonate particle of Embodiment [13] with an acidic composition.

EXAMPLES

The following examples are provided for illustration purposes only and in no way limit the scope of the present disclosure. Embodiments of the present disclosure may employ the use of different or additional components compared to the materials illustrated below, such as other calcium carbonate particles, silicate-based compounds, acids and dispersants, as well as additional components and additives. Embodiments of the present disclosure may also employ the use of different process conditions than the conditions illustrated below for the preparation of silica-coated carbonate particles.

Study Overview

In the examples illustrated below, silica-coated carbonate particles were prepared using different process conditions in order to identify factors that can be used to control and enhance the surface area, mesoporosity and acid resistance of the silica coating. Comparison studies below illustrate that processes of the present disclosure can produce silica-coated carbonate particles in which the surface area and mesoporosity of the silica coating are increased relative to the surface area and mesoporosity of the calcium carbonate particle core. Comparison studies also demonstrate that the magnitude of the increase in surface area, and the proportion of mesoporosity, can be controlled depending upon the identity of the acid and optional dispersant during the coating process.

Materials

Commercial samples of precipitated calcium carbonate (PCC) were used and included Socal® 31 and Socal®92G (both supplied by Imerys PCC France). PCC waste samples supplied by Tate & Lyle and obtained from a sugar (sucrose) refining process were also tested. Commercial sample of ground calcium carbonate (GCC) were also used and included ImerCarb 3L, ImerCarb 5L and IntraCarb 60 slurry (all supplied by Imerys Performance Materials). A liquid sodium silicate ($Na_2O+\sim 4\ SiO_2$) (density=1.35) was obtained from Sigma-Alrich, and contained 7.5-8.5% by weight of $Na_2O$ and 25.5-28.5% by weight of $SiO_2$. Concentrated hydrochloric acid (ACS reagent grade, 37%) was obtained from Sigma-Aldrich. Citric acid (ACS reagent, ≥99.5%) was obtained from Sigma-Aldrich. Sodium hexmetaphosphate (crystalline, +200 mesh, 96%) was obtained from Sigma-Alrich. Deionized water was used to prepare all of the dispersions described below.

Coating Process

The coating process used to prepare the silica-coated carbonate particles of Example 1 is illustrated below with reference to Table 1. The processes of Examples 2-6 were performed in a manner identical to Example 1, except that the conditions were modified as specified in Tables 2 and 3.

TABLE 1

Process Conditions for Silica-Coated Particles vs. Reference PCC

| Sample ID | PCC Base | PCC Slurry Conc. (g/L) | PCC:SiO$_2$ Molar Ratio | Acid Source | Final pH | Aging Time (min) |
|---|---|---|---|---|---|---|
| Reference Sample 1 | Socal ® 31 | N/A | N/A | N/A | N/A | N/A |
| Example 1 | Socal ® 31 | 150 | 3:1 | HCl | 7 | 120 |

An aqueous carbonate slurry was prepared by adding 90 grams of Socal® 31 to 600 mL of deionized water (150 g/L) in a 1 L beaker, and mechanically stirring the resulting mixture for about 5 minutes at ambient temperature (~23° C.). To the stirring aqueous carbonate slurry at ambient temperature was added by dropwise addition (~10 mL/min) an aqueous sodium silicate solution (~1:4 $Na_2O/SiO_2$) such that a resulting molar ratio of calcium carbonate to silica in the resulting carbonate-silicate slurry was 3:1. To the carbonate-silicate slurry under vigorous mechanical stirring at ambient temperature was then added, by dropwise addition, concentrated hydrochloric acid until the pH of the resulting slurry reached a stable pH of 7. The rate of dropwise addition of the hydrochloric acid was adjusted so as to prevent the formation of a viscous gel (especially between pH of 7 and 8). The resulting slurry was then heated to 80° C. under strong mechanical stirring for an aging period of 120 minutes, and the resulting product slurry was filtered through a Büchner funnel with vacuum assistance to obtain an initial filter cake of silica-coated carbonate particles. The initial filter cake was washed with deionized water and then re-dispersed into 500 mL of deionized water, and re-filtered through a Buchner funnel—performing this process two times—to obtain a final filter cake. The final filter cake was then dried in an oven at 120° C. for 12 hours, and milled with a hammer mill to obtain the silica-coated carbonate particles of Example 1.

Silica shells were prepared by acidifying a mechanically-stirred aqueous dispersion of the silica-coated carbonate particles of Example 1 to a pH of 4 using hydrochloric acid, and allowing the acidified dispersion to stir for 1 hour. After this period, the resulting aqueous dispersion was filtered through a Büchner funnel with vacuum assistance to obtain a filter cake of silica shells, which were then washed with deionized water, re-filtered, and dried in an oven at 120° C. for 12 hours.

The Effect of Silica Coating on the Surface Area and BJH Pore Size Distribution of Silica-Coated Calcium Carbonate Particles As used herein "BET surface area" refers to the area of the surface of the particles of the particulate calcium carbonate material with respect to unit mass, determined according to the BET method by the quantity of nitrogen adsorbed on the surface of the particles so as to form a monomolecular layer completely covering the surface (measurement according to the BET method, AFNOR standard X11-621 and 622 or ISO 9277). In certain embodiments, BET surface area is determined in accordance with ISO 9277 or any method equivalent thereto.

As shown in FIG. 1, the BET surface area of the silica-coated carbonate particles of Example 1 (40.7 m$^2$/g) was more than double the BET surface area of the PCC core particles (Reference Sample 1) (19.7 mm$^2$/g). Therefore, it is demonstrated that a coating process of the present disclosure produces a silica coating having a significantly-higher surface area compared to the surface area of the calcium carbonate core particle.

The BJH (Barrett-Joyner-Halenda) pore sizes of the starting PCC particles (Reference Sample 1) and the silica-coated carbonate particles of Example 1 were measure using the BJH model. The BJH model is derived from the same $N_2$ adsorption isotherm that is used by the BET surface area calculations (measurement according to the BET method, AFNOR standard X11-6212 and 622 or ISO 9277). The BJH model is described in Barrett et al., Am. Chem. Soc., 73 (1951), pages 373-380, the contents of which are incorporated herein by reference. A Micromeritics TRISTAR 3000 and Micromeritics VACPREP 061 may, for example, by used. The samples may, for example, be degassed in an oven overnight at 105° C., followed by 180° C. for 30 minutes under nitrogen flow and cooling for 30 minutes under nitrogen flow. The isotherm may, for example, be measured for relative pressures $P/P_0$ ranging from 0.05 to 0.98. Average pore size refers to pore diameter. Porous volume is cumulative and obtained by BJH on the desorption branch for pore sizes between 1.7 and 50 nm. The measured pore volumes versus pore diameters are shown in FIG. 2.

As shown in FIG. 2, the silica-coated carbonate particles of Example 1 exhibited substantially greater mesoporosity compared to the starting PCC particles of Reference Sample 1. Whereas the starting PCC particles of Reference Sample 1 exhibited no maximum peak in the mesoporous range of 2-50 nm along the horizontal axis in FIG. 2, the silica-coated carbonate particles of Example 1 exhibited a maximum peak at approximately 15 nm. Therefore, it is demonstrated that a coating process of the present disclosure produces a silica coating having a significantly higher degree of mesoporosity compared the mesoporosity of the calcium carbonate core particle.

As shown in FIGS. 3(a) through 3(d), the starting PCC particles (Reference Sample 1), the silica-coated carbonate particles of Example 1, and the silica shells of Example 1 were imaged using a scanning electron microscope (SEM) at 25 kV and 50 kV levels of magnification. These images show that the coating process of Example 1 effectively coated the PCC particles with a silica coating robust enough to withstand the acid removal of the calcium carbonate to produce silica shells that maintain the original shape of the starting PCC particles.

As shown in FIGS. 4(a) through 4(f), the starting PCC particles (Reference Sample 1) and the silica-coated carbonate particles of Example 1 were imaged using an SEM at a 25 kV level of magnification, and these samples were also imaged using energy-dispersive X-ray (EDX) mapping showing elementals distributions of both Ca and Si. These images show that the coating process of Example 1 effectively coated the PCC particles with a silica coating that was homogeneously distributed over the surface of the PCC particles.

The Effect of Acid Source on the Surface Area, BJH Pore Size Distribution, and Acid Resistance of Silica-Coated Calcium Carbonate Particles Another study was undertaken the explore the effect that the acid source used during the silica-coating process has on the surface area, BJH pore size distribution and acid resistance of the resulting silica-coated calcium carbonate particles. Table 2 summarizes the process parameters for this study, in which the acid sources hydrochloric acid, carbon dioxide and citric acid were used in Examples 1, 2 and 3, respectively.

TABLE 2

Process Conditions Using Different Acid Sources

| Sample ID | PCC Base | PCC Slurry Conc. (g/L) | PCC:SiO$_2$ Content | Acid Source | Final pH | Aging Time (min) |
|---|---|---|---|---|---|---|
| Reference Sample 1 | Socal ® 31 | N/A | N/A | N/A | N/A | N/A |
| Example 1 | Socal ® 31 | 150 | 3:1 | HCl | 7 | 120 |
| Example 2 | Socal ® 31 | 150 | 3:1 | CO$_2$ | 7 | 120 |
| Example 3 | Socal ® 31 | 150 | 3:1 | Citric Acid | 7 | 120 |

This study showed that use of the weak (higher pKa) organic acid of Example 3 (citric acid) profoundly increases the surface area and mesoporosity of the resulting silica-coated calcium carbonate particles—compared to the use of the strong (low pKa) mineral acid of Example 1 (hydrochloric acid) and the very weak acid of Example 2 (carbon dioxide).

Figure 5:
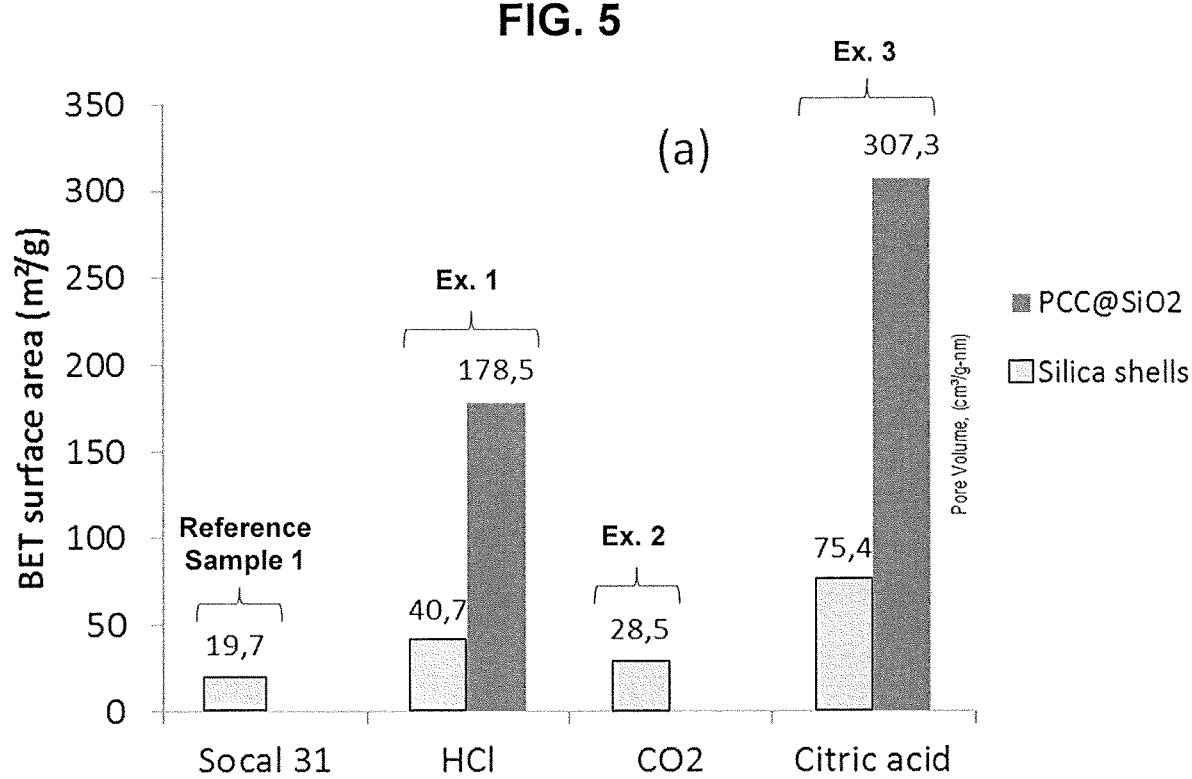
FIG. 5 is a bar chart comparing the specific surface area (obtained by BET) of the commercial PCC Socal® 31 versus the surface areas of silica-coated PCC particles formed from Socal® 31 using different acids, and comparing the surface areas of corresponding silica shells formed by reacting the silica-coated PCC particles with acid.

As shown in FIG. 5, the BET surface area of the silica-coated calcium carbonate particles of Example 3 (citric acid) (~75 m$^2$/g) was much higher than the BET surface areas of the silica-coated particles of Example 1 (hydrochloric acid) (~40 m$^2$/g) and Example 2 (carbon dioxide) (~25 m$^2$/s). The increase in BET surface area for citric acid is even more pronounced for the corresponding silica shells, as shown in FIG. 5. It is clear from this experimental data that citric acid is a more effective acid source in terms of producing a silica coating with increased surface area relative to the starting PCC particles of Reference Sample 1. As described in the study below, it was found that the surface area of a silica-coated calcium carbonate particle formed with hydrochloric acid can be increased by including a dispersant during the formation of the silica coating.

Figure 6:
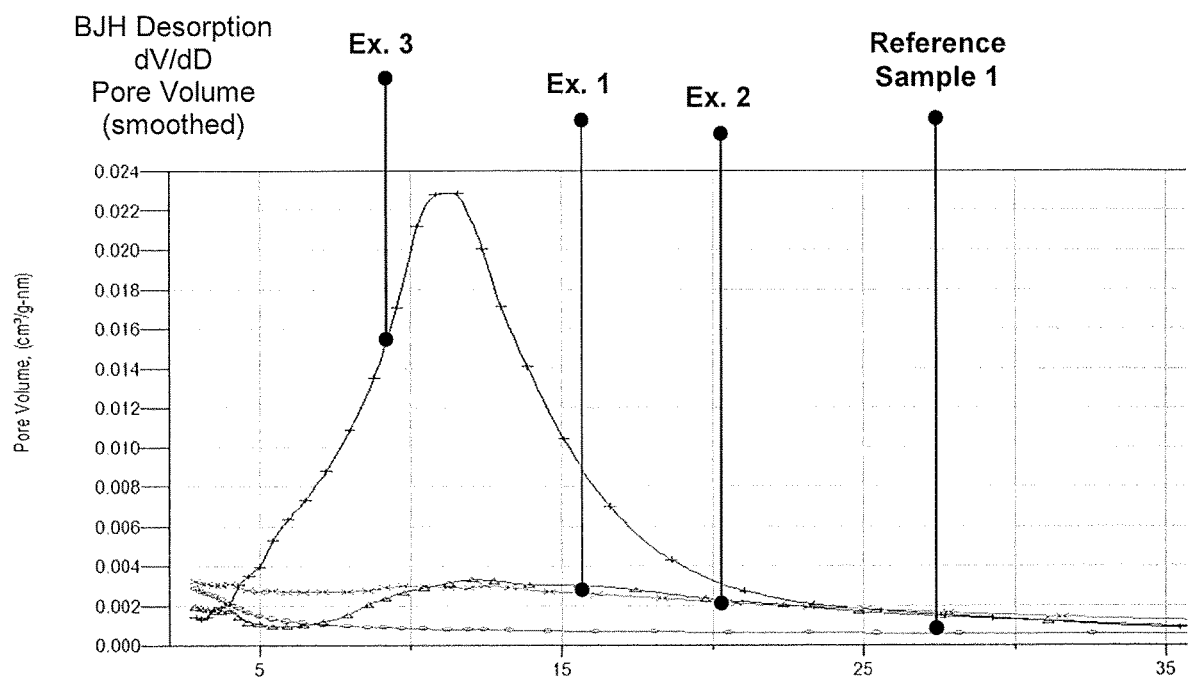
FIG. 6 is a graph that charts pore volume ($cm^3/g \cdot nm$) versus pore diameter (nm) obtained by the BJH method for the commercial PCC Socal® 31 versus silica-coated PCC particles formed from Socal® 31 using different acids.

As shown in FIG. 6, a similar trend was observed with respect to the mesoporosity of the silica-coated calcium carbonate particles of Examples 1, 2 and 3. The use of citric acid as the acid source during the formation of the silica coating resulted in a profound improvement in mesoporosity. The BJH pore size distribution for Example 3 (citric acid) shows a sharp maximum peak at about 12 nm—whereas the pore size distributions for the silica-coated particles of Example 1 (hydrochloric acid) and Example 2 (carbon dioxide) did not show a sharp maximum peak.

Without being bound by any particular theory, it is believed that the profound improvement in mesoporosity that occurred with citric acid was used in Example 3 may be caused by an interaction between citric acid and the carbonate surface of PCC particles—in which the bound citrate may further interact with the silicate and thereby act as a spacer or template that leads to the generation of mesopores.

Figure 7:
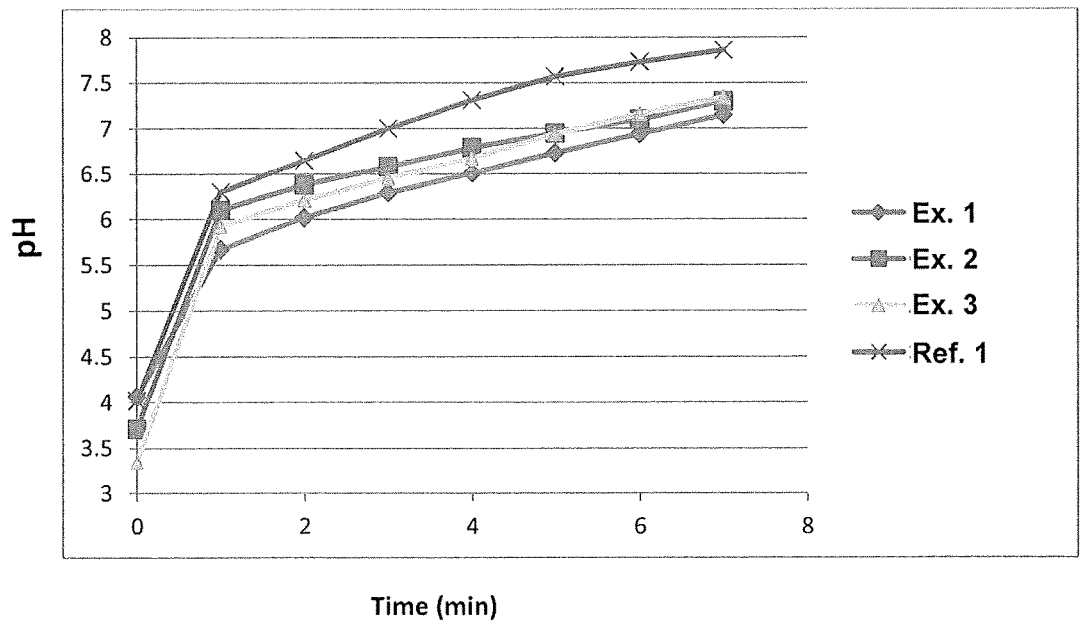
FIG. 7 is an acid resistance graph that charts pH versus time for the commercial PCC Socal® 31 and for silica-coated PCC particles formed from Socal® 31 using different acids.
Figures 8A, 8B, 8C, 8D, 8E, 8F:
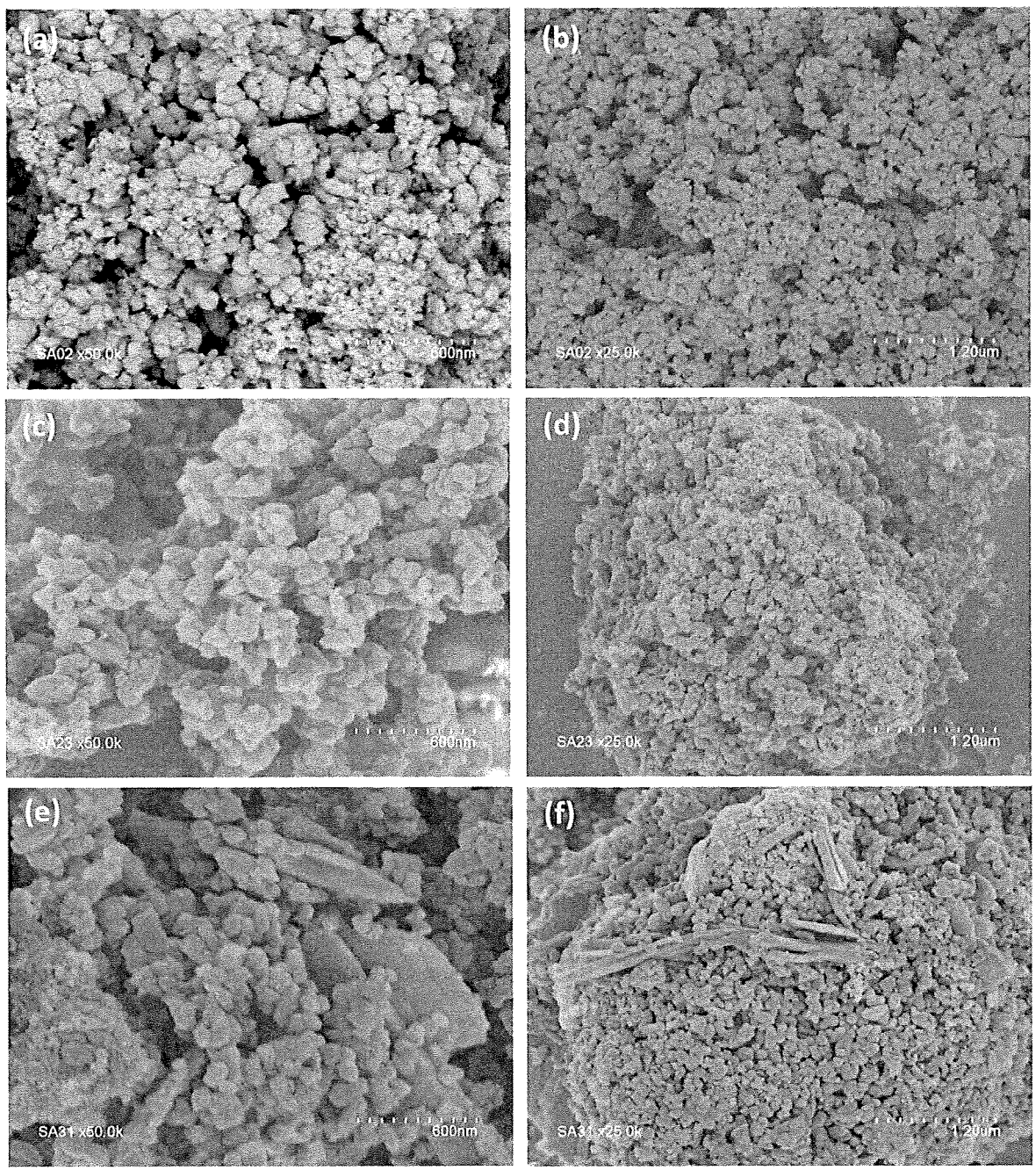
FIG. 8(a) is a SEM micrograph at 50 k magnification of silica-coated PCC particles formed from Socal® 31 using hydrochloric acid.
FIG. 8(b) is a SEM micrograph at 25 k magnification of silica-coated PCC particles formed from Socal® 31 using hydrochloric acid.
FIG. 8(c) is a SEM micrograph at 50 k magnification of silica-coated PCC particles formed from Socal® 31 using $CO_2$.
FIG. 8(d) is a SEM micrograph at 25 k magnification of silica-coated PCC particles formed from Socal® 31 using $CO_2$.
FIG. 8(e) is a SEM micrograph at 50 k magnification of silica-coated PCC particles formed from Socal® 31 using citric acid.
FIG. 8(f) is a SEM micrograph at 25 k magnification of silica-coated PCC particles formed from Socal® 31 using citric acid.

As shown in FIG. 7, when the silica-coated calcium carbonate particles of Examples 1, 2 and 3 were subjected to the acid resistance test described above, the rate of increase in pH was slightly lower for the silica-coated particles of Example 1 (hydrochloric acid)—compared to the rate of increase for the silica-coated particles of Examples 2 (carbon dioxide) and Example 3 (citric acid). This seems to show that the silica coating formed in the presence of hydrochloric acid has greater coverage over the PCC core compared to silica coatings formed in the presence of the other acids. FIG. 7 also includes the acid-resistance data for the starting PCC particles of Reference Sample 1. The rate of pH increase was significantly higher for Reference Sample 1 compared to the silica-coated calcium carbonate particles of Examples 1, 2 and 3.

As shown in FIGS. 8(a) through 8(f), the silica-coated particles of Examples 1, 2 and 3 were imaged using a scanning electron microscope (SEM) at 25 kV and 50 kV levels of magnification. The images of FIGS. 8(e) and 8(f) appear to show the presence of lamellar particles intermixed in the silica coating of Example 3 (citric acid), which are not present in the silica coatings of Example 1 (hydrochloric acid) and Example 2 (carbon dioxide). Without being bound by any particular theory, it is believed that these lamellar particles may be composed of citrate compounds formed by the interaction of citric acid with the calcium carbonate of the PCC particle and/or by the interaction of the resulting citrate with silicates.

The Effect of Dispersant on the Surface Area, BJH Pore Size Distribution, and Acid Resistance of Silica-Coated Calcium Carbonate Particles Another study was undertaken to explore the effect that a dispersant presence during the silica-coating process has on the surface area, BJH pore size distribution and acid resistance of the resulting silica-coated calcium carbonate particles. Table 3 summarizes the process parameters for this study, in which silica-coated calcium carbonate particles were prepared using hydrochloric acid and citric acid both with and without the dispersant sodium hexametaphosphate ((NaPO$_3$)$_6$).

This study showed that performing the silica coating process in the presence of a dispersant profoundly increases the surface area and mesoporosity of the silica coating when hydrochloric acid is used as the acid source—but does not increase the surface area and mesoporosity of the silica coating when citric acid is used as the acid source. The presence of the dispersant does appear to improve the acid resistance of silica-coated particles when either hydrochloric acid or citric acid is used as the acid source.

TABLE 3

Process Conditions Using Different Acids With/Without Dispersant

| Sample ID | PCC Base | Slurry Conc. | PCC:SiO₂ Content | Acid Source | Dispersant | Final pH | Aging Time (min) |
|---|---|---|---|---|---|---|---|
| Ref. Sample 1 | Socal ® 31 | N/A | N/A | N/A | N/A | N/A | N/A |
| Ex. 1 | Socal ® 31 | 150 g/L | 3:1 | HCl | none | 7 | 120 |
| Ex. 4 | Socal ® 31 | 150 g/L | 3:1 | HCl | $(NaPO_3)_6$ | 7 | 120 |
| Ex. 5 | Socal ® 31 | 150 g/L | 3:1 | Citric Acid | none | 7 | 120 |
| Ex. 6 | Socal ® 31 | 150 g/L | 3:1 | Citric Acid | $(NaPO_3)_6$ | 7 | 120 |

Figure 9:
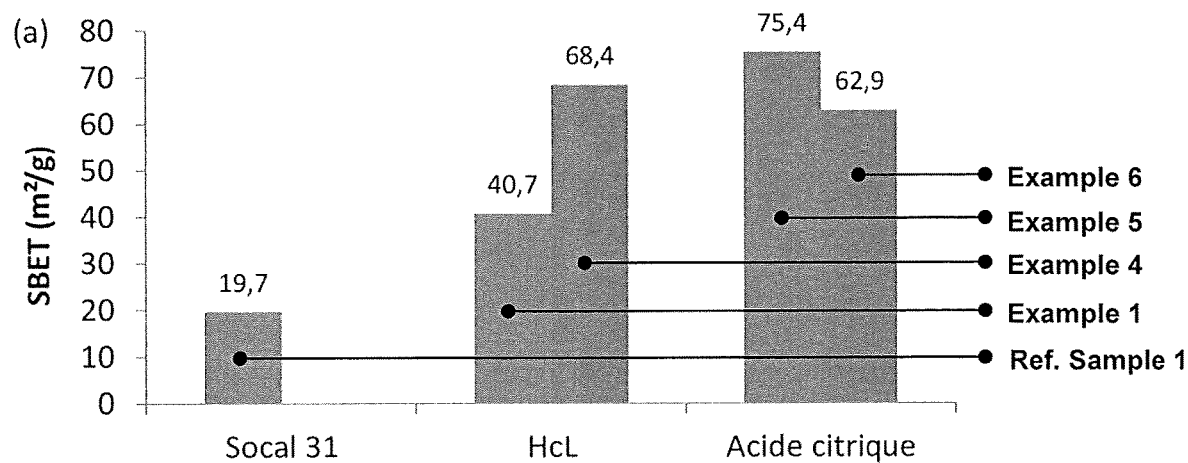
FIG. 9 is a bar chart comparing the specific surface area (obtained by BET) of the commercial PCC Socal® 31 versus the surface areas of silica-coated PCC particles formed from Socal® 31 using different acids both with and without an added dispersant.

As shown in FIG. 9, the BET surface area of the silica-coated particles of Example 4 [HCl+$(NaPO_3)_6$] (68.4 m²/g) was significantly higher than the BET surface area of the silica-coated particles of Example 1 [HCl] (40.7 m²/g)—indicating that the presence of the dispersant sodium hexamethphosphate greatly increases the surface area of the silica coating when hydrochloric acid is used as the acid source. By contrast, the BET surface area of the silica-coated particles of Example 6 [citric acid+$(NaPO_3)_6$] (62.9 m²/g) was lower than the BET surface area of the silica-coated particles of Example 5 [citric acid] (75.4 m²/g)—indicating that the presence of the dispersant sodium hexamethphosphate actually reduces the surface area of the silica coating when citric acid is used as the acid source.

Figure 10:
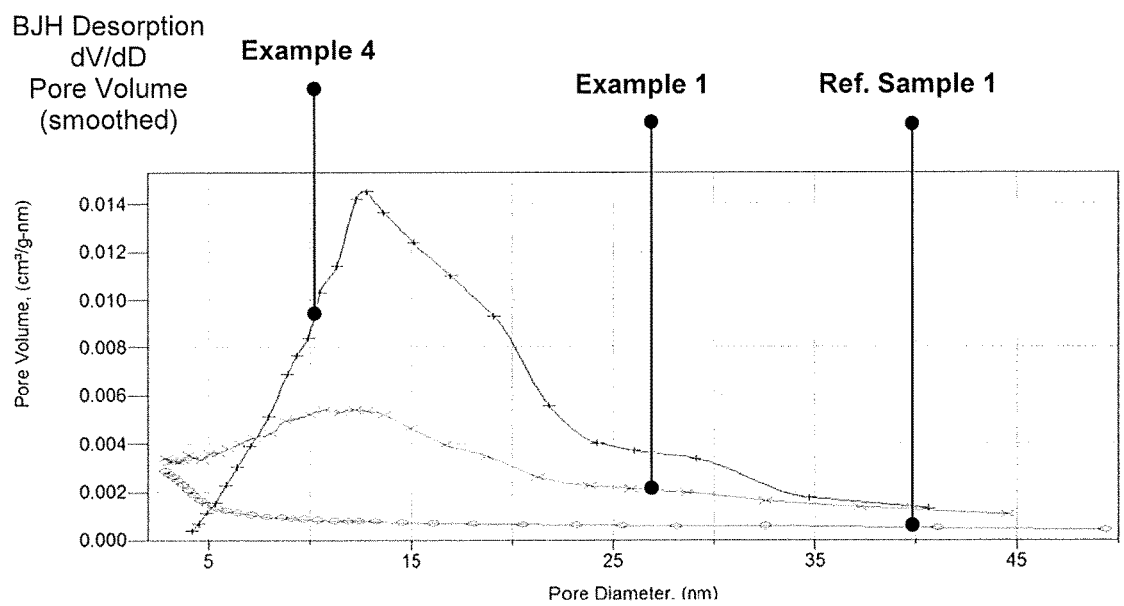
FIG. 10 is a graph that charts pore volume ($cm^3/g \cdot nm$) versus pore diameter (nm) obtained by the BJH method for the commercial PCC Socal® 31 versus silica-coated PCC particles formed from Socal® 31 using HCl both with and without an added dispersant.
Figures 11A, 11B, 11C, 11D:
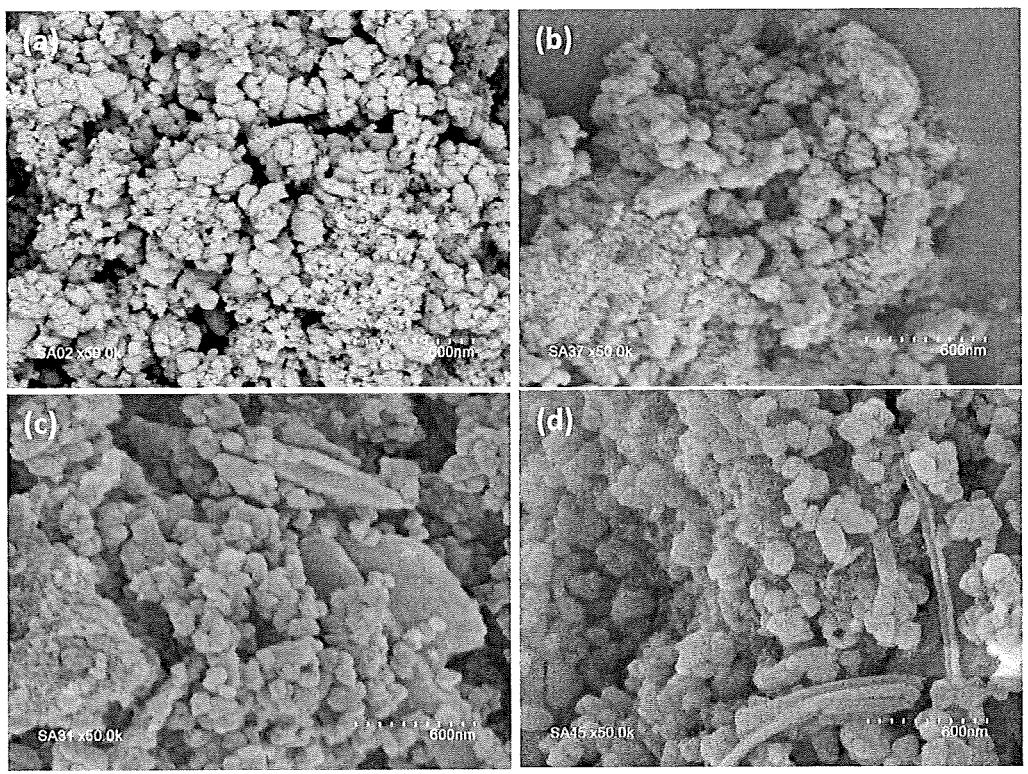
FIG. 11(a) is a SEM micrograph at 50 k magnification of silica-coated PCC particles formed from Socal® 31 using hydrochloric acid without an added dispersant.
FIG. 11(b) is a SEM micrograph at 50 k magnification of silica-coated PCC particles formed from Socal® 31 using hydrochloric acid with an added dispersant.
FIG. 11(c) is a SEM micrograph at 50 k magnification of silica-coated PCC particles formed from Socal® 31 using citric acid without an added dispersant.
FIG. 11(d) is a SEM micrograph at 50 k magnification of silica-coated PCC particles formed from Socal® 31 using citric acid with an added dispersant.

As shown in FIG. 10, the silica-coated particles of Example 4 [HCl+$(NaPO_3)_6$] exhibited a much sharper distribution of mesoporosity compared to the silica-coated particles of Example 1 [HCl]—indicating that the presence of the dispersant sodium hexamethphosphate greatly increases the mesoporosity of the silica coating when hydrochloric acid is used as the acid source.

As shown in FIGS. 11(a) through 11(d), the silica-coated particles of Examples 1, 4, 5 and 6 were imaged using a scanning electron microscope (SEM) at 50 kV levels of magnification. The images of FIGS. 11(c) and 11(d) appear to show the presence of lamellar particles intermixed in the silica coating of Example 5 [citric acid] and Example 6 [citric acid+$(NaPO_3)_6$]. It is noteworthy that fewer of these lamellar particles appear to exists in the image of FIG. 11(d)—corresponding to Example 6 [citric acid+$(NaPO_3)_6$]. Without being bound by any particular theory, it is theorized that the presence of the dispersant sodium hexametaphosphate may cause the observed reduction in BET surface area for Example 6 by reducing the formation of the citrate compounds formed by the interaction of citric acid with the calcium carbonate of the PCC particle and/or by the interaction of the resulting citrate with silicates.

Figure 12:
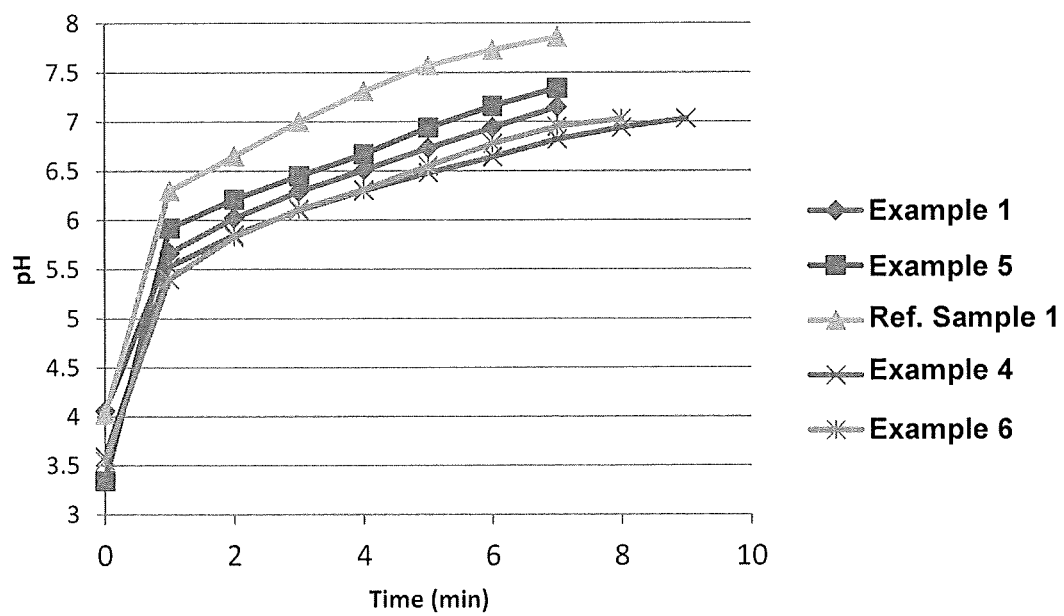
FIG. 12 is an acid resistance graph that charts pH versus time for the commercial PCC Socal® 31 and for silica-coated PCC particles formed from Socal® 31 using different acids both with and without an added dispersant.

As shown in FIG. 12, when the silica-coated calcium carbonate particles of Examples 1 and 4-6 were subjected to the acid resistance test described above, the rates of increase in pH was significantly lower for the silica-coated particles of Example 4 [HCl+$(NaPO_3)_6$] and Example 6 [citric acid+$(NaPO_3)_6$]—compared to the rates of increase in pH for the silica-coated particles of Example 1 [HCl] and Example 5 [citric acid]. Therefore, this data indicates that the silica coatings formed in the presence of the dispersant sodium hexametaphosphate have greater coverage over the PCC core compared to silica coatings formed in the absence of this dispersant.

The above description is presented to enable a person skilled in the art to make and use the invention, and is provided in the context of a particular application and its requirements. Various modifications to the embodiments disclosed herein will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the disclosure may not show every benefit of the invention, considered broadly.

What is claimed is:

1. A process, comprising:
preparing an aqueous carbonate slurry comprising calcium carbonate particles;
adding at least one silicate composition to the aqueous carbonate slurry to obtain a carbonate-silicate slurry;
lowering a pH of the carbonate-silicate slurry by adding at least one acidic compound to obtain a pH-adjusted slurry comprising silica-coated calcium carbonate particles; and
isolating the silica-coated calcium carbonate particles,
wherein:
the silicate composition comprises a silica and a metal oxide;
a molar ratio of the silica to the metal oxide in the silicate composition ranges from 1.1:1 to 5:1;
the adding of the at least one acidic compound is controlled such that a final pH of the pH-adjusted slurry ranges from about 7 to about 10;
the silica-coated calcium carbonate particles comprise a porous coating having an average pore diameter ranging from 2 nm to 50 nm; and
the acidic compound is a water-soluble carboxylic acid.

2. The process according to claim 1, wherein the calcium carbonate particles are selected from the group consisting of precipitated calcium carbonate particles, ground calcium carbonate particles, waste calcium carbonate particles, and mixtures thereof.

3. The process according to claim 1, wherein the calcium carbonate particles are at least partially coated with an organic compound comprising at least one hydroxyl group.

4. The process according to claim 1, further comprising adding a dispersant to at least one of:
the aqueous carbonate;
the carbonate-silicate slurry; and
the pH-adjusted slurry.

5. The process according to claim 1, wherein:
the silicate composition comprises the silica and an oxide of at least one metal selected from the group consisting of an alkali metal and an alkaline earth metal; and
a molar ratio of the silica to the calcium carbonate in the carbonate-silicate slurry ranges from 1:1 to 1:100.

6. The process according to claim 1, wherein the water-soluble carboxylic acid is chosen from the group consisting of formic acid, glyoxylic acid, oxalic acid, glycolic acid, malonic acid, 3-hydroxypropanoic acid, lactic acid, glyceric acid, fumaric acid, maleic acid, oxaloacetic acid, 3-butenoic acid, crotonic acid, methylmalonic acid, succinic acid, malic acid, tartaric acid, dihydroxytartaric acid, butanoic acid, 3-hydroxybutanoic acid, 4-hydroxybutanoic acid, 1,1-cyclopropanedicarboxylic acid, itaconic acid, mesaconic acid, dimethylmalonic acid, glutaric acid, methylsuccinic acid, pentanoic acid, ascorbic acid, citric acid, isocitric acid, 3-methylglutaric acid, and hexanoic acid.

7. The process according to claim 1, wherein the adding of the at least one acidic compound to the carbonate-silicate slurry is controlled such that the final pH of the pH-adjusted slurry ranges from about 7 to about 7.5.

8. The process according to claim 1, further comprising:
aging the at least partially neutralized carbonate-silicate slurry at a temperature ranging from 15° C. to 95° C. over a period ranging from 10 minutes to 120 minutes.

9. The process according to claim 1, wherein the isolating comprises filtering, washing, drying and milling the silica-coated carbonate particles.

10. The process according to claim 1, wherein:
the isolating comprises filtering, washing, drying and milling the silica-coated carbonate particles, such that the washing comprises at least one of
(i) washing a filter cake of the silica-coated calcium carbonate particles with a washing liquid, and
(ii) dispersing the silica-coated carbonate particles into the washing liquid, filtering the silica-coated carbonate particles from the washing liquid; and
the washing liquid comprises water and optionally a dispersant or detergent.

11. The process of claim 1, wherein the silica-coated calcium carbonate particles have a BET surface area ranging from about 50 $m^2/g$ to about 75 $m^2/g$; and wherein the porous coating has an average pore diameter ranging from 5 nm to 20 nm.

12. The process of claim 1, wherein the ratio of the BET surface area of the silica-coated particle over the BET surface area of a calcium carbonate particle precursor of the calcium carbonate core ranges from 2:1 to 6:1.

13. The process according to claim 4, wherein the dispersant is added to at least one of the aqueous carbonate and the carbonate-silicate slurry prior to or during pH adjustment; wherein the dispersant is a water-soluble salt capable of supplying anionic species.

* * * * *